(12) United States Patent
Merkel et al.

(10) Patent No.: US 9,266,094 B2
(45) Date of Patent: Feb. 23, 2016

(54) CATALYST AND METHOD FOR PRODUCING AROMATIC AMINES IN THE GAS PHASE

(75) Inventors: Michael Merkel, Düsseldorf (DE); Karl-Heinz Wilke, Moers (DE); Peter Lehner, Baytown, TX (US)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/240,056

(22) PCT Filed: Aug. 29, 2012

(86) PCT No.: PCT/EP2012/066749
§ 371 (c)(1),
(2), (4) Date: Apr. 21, 2014

(87) PCT Pub. No.: WO2013/030221
PCT Pub. Date: Mar. 7, 2013

(65) Prior Publication Data
US 2014/0309457 A1     Oct. 16, 2014

(30) Foreign Application Priority Data
Aug. 31, 2011   (DE) .......................... 10 2011 081 897

(51) Int. Cl.

| | | |
|---|---|---|
| B01J 23/648 | (2006.01) | |
| C07C 209/36 | (2006.01) | |
| B01J 37/02 | (2006.01) | |
| B01J 23/62 | (2006.01) | |
| B01J 23/64 | (2006.01) | |
| B01J 35/00 | (2006.01) | |
| B01J 35/10 | (2006.01) | |
| B01J 27/055 | (2006.01) | |
| B01J 27/10 | (2006.01) | |
| B01J 37/16 | (2006.01) | |
| B01J 37/18 | (2006.01) | |

(52) U.S. Cl.
CPC .............. *B01J 23/6482* (2013.01); *B01J 23/62* (2013.01); *B01J 23/64* (2013.01); *B01J 27/055* (2013.01); *B01J 27/10* (2013.01); *B01J 35/002* (2013.01); *B01J 35/1009* (2013.01); *B01J 35/1014* (2013.01); *B01J 37/0205* (2013.01); *B01J 37/0207* (2013.01); *C07C 209/36* (2013.01); *B01J 37/16* (2013.01); *B01J 37/18* (2013.01); *B01J 2523/00* (2013.01); *Y02P 20/52* (2015.11)

(58) Field of Classification Search
CPC .. B01J 23/6482; B01J 2523/00; C07C 209/36
See application file for complete search history.

(56) References Cited

U.S. PATENT DOCUMENTS

| | | | |
|---|---|---|---|
| 3,636,152 A | | 1/1972 | Szigeth |
| 4,265,834 A | | 5/1981 | Birkenstock et al. |
| 5,097,071 A | | 3/1992 | Immel et al. |
| 5,144,076 A | * | 9/1992 | Krishnamurti et al. ....... 564/417 |
| 5,808,157 A | | 9/1998 | Langer et al. |
| 5,877,350 A | | 3/1999 | Langer et al. |
| 6,043,394 A | | 3/2000 | Langer et al. |
| 6,080,890 A | | 6/2000 | Langer et al. |
| 6,562,749 B1 | * | 5/2003 | Lednor et al. ................... 502/66 |
| 7,692,042 B2 | | 4/2010 | Dugal et al. |
| 8,455,691 B2 | | 6/2013 | Sommer et al. |
| 2007/0238901 A1 | | 10/2007 | Dugal et al. |
| 2008/0234518 A1 | | 9/2008 | Sommer et al. |

FOREIGN PATENT DOCUMENTS

| | | |
|---|---|---|
| DE | 2848014 A1 | 5/1980 |
| DE | 3007202 A1 | 9/1981 |
| EP | 507118 A2 | 10/1992 |
| EP | 1670747 B1 | 5/2009 |
| JP | 2007217405 A | 8/2007 |

* cited by examiner

*Primary Examiner* — Clinton Brooks
(74) *Attorney, Agent, or Firm* — Donald R. Palladino; Robert S. Klemz

(57) ABSTRACT

The present invention relates to a catalyst comprising a ceramic support with a BET surface area of less than 40 m²/g and (a) 1.0 to 100 g of at least one metal of groups 8 to 12 of the periodic table of the elements, (b) 1.0 g to 100 g of at least one metal of groups 4 to 6 and 12 of the periodic table of the elements and (c) 1.0 g to 100 g of at least one metal of groups 14 and 15 of the periodic table of the elements per liter of bulk volume of the ceramic support, wherein the catalyst is additionally doped with (d) potassium in a content of from 0.0050% by weight to 0.20% by weight, based on the total weight of the catalyst. The present invention also provides the use of such a catalyst in the catalytic gas phase hydrogenation of nitroaromatics.

7 Claims, No Drawings

CATALYST AND METHOD FOR PRODUCING AROMATIC AMINES IN THE GAS PHASE

The present invention relates to a catalyst comprising a ceramic support with a BET surface area of less than 40 m²/g and (a) 1.0 g to 100 g of at least one metal of groups 8 to 12 of the periodic table of the elements, (b) 1.0 g to 100 g of at least one metal of groups 4 to 6 and 12 of the periodic table of the elements and (c) 1.0 g to 100 g of at least one metal of groups 14 and 15 of the periodic table of the elements per liter of bulk volume of the ceramic support, wherein the catalyst is additionally doped with (d) potassium in a content of from 0.0050% by weight to 0.20% by weight, based on the total weight of the catalyst. The present invention also provides the use of such a catalyst in the catalytic gas phase hydrogenation of nitroaromatics.

The hydrogenation of nitrobenzene to give the corresponding aromatic amines in the gas phase on fixed-location palladium catalysts on ceramic supports is known. DE 28 49 002 A1 thus describes a process for the reduction of nitro compounds in the presence of palladium-containing three-component supported catalysts in cooled tube reactors. In preferred embodiments, the catalyst contains 1 to 20 g of palladium, 1 to 20 g of vanadium and 1 to 20 g of lead per liter of α-Al₂O₃. Similar catalysts, although additionally doped with Mo, Re or W, have also been described in DE 197 15 746 A1. EP 1 882 681 A1 discloses that it is advantageous additionally to dope such three-component supported catalysts with a sulfur- or phosphorus-containing, preferably phosphorus-containing, compound. In this context, contents of from 0.1 to 2% by weight, preferably from 0.1 to 1% by weight of sulfur or phosphorus are disclosed. Examples of phosphorus-containing compounds which are mentioned are the oxygen acids of phosphorus or alkali metal salts thereof, such as e.g. sodium dihydrogen phosphate, sodium or potassium phosphate or sodium hypophosphite. In this context, no particular importance is attributed to the counter-ion potassium.

A disadvantage of the gas phase hydrogenations described in the patent publications mentioned is the formation of phenolic by-products. Thus, for example, for the simplest aromatic amine, aniline, considerable outlay is involved to separate of the by-product phenol, the boiling temperature of which of 182° C. differs from that of aniline by only 2 K (see e.g. EP 1 670 747 B1, EP 2 028 176 A1, JP 2007 217405 (A), EP 1 845 079 A1, EP 1 845 080 A1). The majority of the aniline produced worldwide is used for the preparation of methylenediphenyldiamine (MDA) for the preparation of methylenediphenyl-diisocyanate (MDI). If the phenol is not separated off beforehand, it contaminates the waste water in the MDA process and must then be destroyed in a suitable waste water treatment similarly requiring outlay (e.g. active charcoal treatment, ozonolysis etc.).

There was therefore a need for a process for the preparation of aromatic amines in the gas phase by catalytic hydrogenation of the corresponding nitro compounds, in which the formation of phenolic compounds is largely suppressed by the use of a specific catalyst, without other factors, such as the operating time of the catalyst, thereby deteriorating, so that the outlay for separating off or destroying these phenolic compounds is reduced.

Taking into account this need, the present invention provides a catalyst comprising a ceramic support with a BET surface area of less than 40 m²/g, preferably less than 20 m²/g, particularly preferably less than 10 m²/g, and (a) 1.0 g to 100 g, preferably 1.0 g to 50 g of at least one metal of groups 8 to 12 of the periodic table of the elements, preferably Pd, Pt, (b) 1.0 g to 100 g, preferably 1.0 g to 50 g of at least one metal of groups 4 to 6 and 12 of the periodic table of the elements, preferably Ti, V, Nb, Ta, Cr, Mo, W, and (c) 1.0 g to 100 g, preferably 1.0 g to 20 g of at least one metal of groups 14 and 15 of the periodic table of the elements, preferably Pb, Bi, per liter of bulk volume of the ceramic support, wherein the catalyst is doped with (d) potassium in a content of from 0.0050% by weight to 0.20% by weight, preferably 0.050% by weight to 0.15% by weight, particularly preferably from 0.070% by weight to 0.12% by weight, based on the total weight of the catalyst.

The present invention also provides a process for the preparation of aromatic amines of the formula

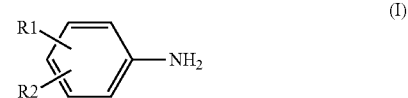

in which R1 and R2 independently of each other denote hydrogen, methyl or ethyl, wherein R1 can additionally denote NH₂, by hydrogenation of nitroaromatics of the formula

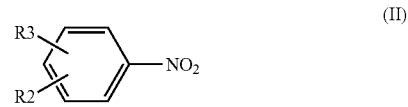

in which R2 and R3 independently of each other denote hydrogen, methyl or ethyl, wherein R3 can additionally denote NO₂, with hydrogen in the presence of the catalyst according to the invention.

In this context, a ceramic support is understood as meaning any ceramic solid which meets the specified BET surface area requirements. Ceramic supports which are suitable in particular are: metal oxides, mixed metal oxides (i.e. oxides of two or more metals) or mixtures of metal oxides and mixed metal oxides of the elements chosen from the group of magnesium, aluminium, silicon, germanium, zirconium and titanium. α-Aluminium oxide is particularly preferably employed as the support material.

The criterion for the BET surface area is the value determined in accordance with DIN ISO 9277 (May 2003).

The bulk volume of the support is calculated from the bulk density of the support determined in accordance with EN ISO 60, by the formula "bulk volume=weight/bulk density". The amounts stated for components (a) to (c) in g per liter of bulk volume relate to the metals as such (and not, for example, to their oxides). However, this is not to say that the metals are necessarily present in elemental form on the support. If several representatives of a component (a) to (c) are present, the amounts stated in g per liter of bulk volume of the support in each ease relate to the sum of all the representatives of a component (a) to (c), i.e. if, for example, lead and bismuth are present as component (c), the total content of these two components is between 1.0 g and 100 g, preferably between 1.0 g and 20 g, particularly preferably between 2.0 g and 10 g per liter of the hulk volume of the support.

In the context of the present invention, the group designations for the periodic table of the elements are in line with the IUPAC recommendation of 1986.

The doping element potassium (d) is introduced into the catalyst in the form of a potassium salt containing potassium ions (see below for details). The chemical nature of the anion of the potassium salt may change in the course of time, depending on the conditions under which the catalyst is used. The amounts stated for the doping element potassium (d) in % by weight relate to potassium as such (that is to say not to the potassium salt employed in the preparation).

Embodiments of the invention are described in the following. In this context, various embodiments can be combined with one another as desired, if the opposite does not clearly emerge from the context.

Methods for the preparation of the noble metal supported catalysts according to the invention are known in principle. Preferably, a catalyst precursor compound comprising the ceramic support and components (a) to (c) is first prepared as described in DE 28 49 002 A1, in particular on p. 12, 1. 1 to p. 13, 1. 16, the catalyst not necessarily having to be dried first in the reactor. In this context, the pretreatment of the support material with a base is indeed preferred, but not absolutely necessary. It has proved advantageous if the active components of the catalyst are present precipitated in a narrow zone as close as possible to the surface of support shaped bodies and the inside of the support material contains no metal.

The metals can be applied to the support individually or as a mixture in the form of solutions of their salts. Suitable salts are, for example, the halides, acetates, carbonates, bicarbonates, sulfates, phosphates, oxalates, formates, oxides and hydroxides. After each impregnation operation and/or at the end, a reduction is carried out, for which hydrogen, hydrazine and/or formic acid is employed.

In principle, the supported catalysts according to the invention can have any desired form, such as spheres, rods, Raschig rings, granules or tablets. Preferably, shaped bodies which in bulk form have a low flow resistance with good gas-surface contact, such as Raschig rings, saddle bodies, wagon wheels and/or spirals, are used. Particularly preferably, catalyst shaped bodies which are essentially spherical and have a weight-related average particle size $x_{50.3}$, determined by sieve analysis (DIN 66 165 of April 1987), of between 1.0 mm and 10 mm are used. The catalysts according to the invention can be employed in the pure form or in a dilution with other inert packing, e.g. of glass, ceramic or metal.

After production of the catalyst precursor compound comprising components (a) to (c) on a ceramic support, doping with potassium is carried out. For this, the catalyst precursor compound is impregnated with an aqueous solution of a potassium salt such that the solution is absorbed completely. If necessary, the absorbency of the catalyst precursor compound is to be determined in preliminary experiments (in general this corresponds to the absorbency of the support, so that this can be employed for the preliminary experiments). The wet catalyst is then dried to constant weight. This can be effected in an oven at temperatures of between 50° C. and 200° C., preferably between 100° C. and 150° C., and/or in a stream of hot air or of a hot inert gas.

Preferred potassium salts for the doping are those which have a high potassium content (based on the formula weight) and which are commercially available and readily soluble in water and have a low toxicity, if any, in particular potassium sulfate, potassium chloride, potassium hydroxide, potassium carbonate, potassium bicarbonate, potassium bromide, potassium acetate, potassium formate and/or potassium nitrate. Catalysts in which the doping element potassium (d) has been introduced in the form of potassium sulfate or potassium chloride are preferred.

A catalyst comprising α-aluminium oxide with a BET surface area of less than 10 m²/g as the support and
  (a) 8.0 g-50 g of palladium,
  (h) 8.0 g-50 g of vanadium,
  (c) 2.0 g-1.0 g of lead
  per liter of bulk volume of the α-aluminium oxide,
wherein the catalyst is doped with
  (d) potassium in a content of from 0.070% by weight to 0.12% by weight, based on the total weight of the catalyst,
is particularly preferred.

The catalysts according to the invention described above are suitable as catalysts for continuous gas phase hydrogenations of nitro compounds of the general formula II

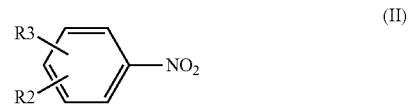

(II)

in which R2 and R3 independently of each other denote hydrogen, methyl or ethyl, wherein R3 can additionally denote NO₂. In this context, in certain embodiments unreacted hydrogen (and any dilution gases added, see below) can be recycled into the reaction (circulating gas procedure), if necessary after sluicing out a small part stream for the purpose of avoiding accumulation of undesirable constituents. Preferably, in the context of the present invention aniline is prepared by hydrogenation of nitrobenzene. It is found here that a considerably smaller amount of phenol is formed as a by-product, without the operating time of the catalyst being significantly impaired. Since phenol is particularly difficult to remove from aniline by distillation, this is a beneficial effect even if the formation of other phenolic compounds like aminophenol is not affected or even slightly increased.

In this context, the gas phase hydrogenation is preferably carried out by a process in which the catalyst is arranged in a stationary bed. However, the use of mobile catalysts, for example in a fluidized bed or migrating bed process, is likewise possible. The process procedure is either isothermal (i.e. with removal as far as possible of the resulting heat of reaction by a cooling medium, for example by a heat transfer oil in a tube bundle reactor) or adiabatic (i.e. in insulated reactors without devices for removal of heat, in which the heat of reaction is discharged with the reaction gases). The isothermal process is preferred. Examples of isothermal processes in which the catalyst according to the invention can be employed are to be found, inter alia, in EP 0 011 090 A1, DE 19 715 746 A1 and EP 0 944 578 B1. Adiabatic processes in which the catalyst according to the invention can be employed are described in EP 0 696 573 B1, EP 0 696 574 B1 and in particular in EP 1 882 681 A1.

The vaporization of the nitroaromatic can be carried out according to the prior art in known evaporators, such as e.g. falling film, ascending tube, injection, thin film, circulating and coiled tube evaporators. The vaporization can be followed by a mist collection which is known in principle. In the circulating gas procedure, metering in of the nitroaromatic can be carried out as described in DE-OS-1 809 711, but the nitroaromatic is preferably vaporized completely in the fresh hydrogen and then introduced into the circulating gas stream in gaseous form. The advantage of this procedure lies in the significantly lower formation of deposits in the reactor and in the feed lines. The educt gas stream is mixed in a known manner by means of an appropriate feed and distribution and/or by mixing devices in the circulating stream.

Atomization of the liquid nitroaromatic into the fresh hydrogen or circulating gas/hydrogen stream by means of one-component or two-component nozzles is furthermore possible, it being possible for the educt gas stream to be combined after superheating in a heat exchanger.

The molar ratio of hydrogen to nitro groups to be employed depends on the procedure. In the isothermal process, according to the invention the molar ratio of hydrogen to nitro groups is 3:1 to 30:1, preferably 4:1 to 20:1, particularly preferably 5:1 to 10:1. In the adiabatic process, according to the invention the molar ratio of hydrogen to nitro groups is 3:1 to 150:1, preferably 6:1 to 125:1, very particularly preferably 12:1 to 100:1 and exceptionally very particularly preferably 50:1 to 90:1.

The hydrogen concentration can be lowered here by admixing inert gases, such as nitrogen, helium, argon and/or steam. Preferably, nitrogen is admixed as an inert gas. Up to 10 mol, preferably up to 3 mol, particularly preferably up to 1 mol of inert dilution gas can be admixed per mol of hydrogen. In adiabatic processes it is to be remembered that the heat of reaction must be discharged with the reaction gases, i.e. if low molar ratios of hydrogen to nitro groups are to be employed, the dilution gases mentioned must be added in an amount sufficient to keep the adiabatic jump in temperature within limits such that the maximum catalyst temperature (see below) is not exceeded.

Reactors which can be employed for the process according to the invention in the isothermal mode of operation are all known reactors which are suitable for gas phase reactions with cooled stationary catalyst beds. Suitable reactors are e.g. tube bundle reactors, in which the catalyst is within tubes around which a heat transfer medium flows, and reactors in which, conversely, the heat transfer medium flows within the tubes and the catalyst is outside the tubes. Such reactors are known, for example, from DE 28 4 014 A1 and DE 30 07 202 A1. In the process according to the invention, the length of the catalyst bed in the direction of flow is 0.5 to 20 m, preferably 1 m to 10 m, particularly preferably 2 m to 6 m. The length of the bed can optionally also be achieved by several reactors connected in series.

Reactors which can be used for the process according to the invention in the adiabatic mode of operation are simple reactors in which the catalyst is arranged in the form of a bed between simple support grids and/or metal screens. A heat transfer medium circulation within the reactor is dispensed with completely, since the reaction enthalpy—possibly apart from minor, unavoidable heat losses—is reflected quantitatively in the temperature difference between the educt and product gas stream. Reactors of such a type are inexpensive and robust in all sizes.

The process according to the invention is operated at maximum catalyst temperatures of 600° C., preferably 550° C., particularly preferably 500° C. and exceptionally particularly preferably 460° C. This applies equally to the isothermal and adiabatic procedure. The maximum catalyst temperature in the isothermal process relates to short-term temperature peaks (so-called hotspots) in the catalyst bed, which cannot always be avoided on a large industrial scale even with optimized cooling circulations. Such temperature peaks are cooled down again rapidly, however, so that in the isothermal process the exit temperature of the product gas mixture is essentially equal to the entry temperature of the educt gas mixture. The entry temperature of the gaseous reaction mixture is between 200° C. and 460° C., preferably between 210° C. and 440° C., particularly preferably between 215° C. and 300° C. and exceptionally particularly preferably between 220° C. and 260° C. This applies equally to the isothermal and adiabatic procedure. In the isothermal process, it may be advantageous if the temperature of the cooling medium is raised continuously or stepwise during a running period (see below).

In the preferred use of stationary catalyst beds, after a certain period of time (operating time) the catalyst employed is deactivated to the extent that satisfactory conversion of nitro compound is no longer achieved. The reaction is then interrupted and the catalyst is regenerated. When the regeneration has taken place, the reaction can be started up again in a new running period.

The regeneration of deactivated catalyst beds is carried out with nitrogen/air mixtures at temperatures of from 200° C. to 400° C., preferably at 250° C. to 350° C., without dismantling the catalyst from the reactor. This regeneration is in general started at nitrogen contents of from 85 vol. % to 100 vol. % in the gas stream, and the oxygen content is raised stepwise to the content of pure air during the burning off. If necessary, persistent coking deposits can be burned off with pure oxygen at the end of the regeneration. Instead of nitrogen, other inert gases can also be admixed to oxygen or air, such as argon, helium and/or steam.

The dilution, which is conventional in certain embodiments, of the reaction mixture with an inert gas is preferably applied at the start of a running period with fresh catalyst and after the regeneration of the catalyst by burning off with air and reduction with hydrogen. Preferably, the mixture is diluted with an inert gas in the first 300 hours, particularly preferably in the first 200 hours, in particular in the first 100 hours after starting up again.

In the preferred isothermal procedure, the absolute total pressure on entry into the reactor is between 0.500 bar and 6.00 bar, preferably between 1.10 bar and 3.00 bar, particularly preferably between 1.20 bar and 2.00 bar. In the adiabatic procedure, the absolute total pressure on entry into the reactor is between 1.00 bar and 50.0 bar, preferably between 2.00 bar and 20.0 bar, particularly preferably between 2.00 bar and 10.00 bar.

The loading of the catalysts according to the invention with the aromatic nitro compound employed should be increased continuously or stepwise from 0.010 $kg_{nitro\ compound}/(l_{catalyst} \cdot h)$ to 0.20 $kg_{nitro\ compound}/(l_{catalyst} \cdot h)$ up to 0.50 $kg_{nitro\ compound}/(l_{catalyst} \cdot h)$, to 5.0 $kg_{nitro\ compound}/(l_{catalyst} \cdot h)$, the maximum loading being reached within 10 to 1,000 hours. The term "$l_{catalyst}$" in this context relates to the bulk volume of the catalyst, which in this case is identical to the internal volume of the part of the reactor filled with catalyst.

The high final loading is kept constant until unreacted nitro compound breaks through. If the educt concentration assumes too high a value at the end of the reactor, in the isothermal procedure the temperature of the heat transfer medium can be raised. Alternatively or additionally, the loading of nitro compound can also be lowered, in order to delay an interruption in production for regeneration of the catalyst. The latter possibility can of course also be applied to the adiabatic procedure. Further possibilities in the adiabatic procedure include raising the entry temperature and allowing a higher jump in temperature. When a "too high" value of nitroaromatic in the product stream is reached depends on the concrete conditions of a production plant, for example the capacity of the downstream distillation or also the intended field of use of the aromatic amine. Under certain circumstances it may be appropriate already to carry out one or more of the measures described at the first signs of unreacted nitroaromatic in the product (i.e. of the order of 10 ppm of nitroaromatic).

The technical realization of the process with the catalysts according to the invention can be, for example, as follows: A circulating gas stream, essentially comprising hydrogen and a little water, is compressed in order to overcome the flow resistances of the plant. The gas stream is heated up by means of counter-current heat exchange, the heat being removed e.g. from the circulating gas stream before condensation of the products. The circulating gas stream is brought to the desired temperature. In the fresh hydrogen which replaces that consumed, the nitroaromatic to be hydrogenated is vaporized, superheated and then mixed with the circulating gas stream. The gas mixture is passed into a thermostatically controlled reactor (e.g. tube bundle reactor) with a catalyst arranged in a stationary form (isothermal procedure) or into a well-insulated reactor without a device for removal of heat (adiabatic procedure). The heat of reaction liberated is removed from the reactor by means of a heat transfer medium (e.g. heat transfer oil or salt melt) in the isothermal procedure; in the adiabatic procedure it is reflected in a corresponding increase in the temperature of the product gas stream (adiabatic jump in temperature). The product stream leaving the reactor is used to heat up the circulating gas stream and then cooled until the amine formed and water condense. The liquids are discharged, as is a small amount of circulating gas for removal of inert gases, e.g. nitrogen or ammonia, which would otherwise become concentrated. The circulating gas is then fed to the compressor again.

The process according to the invention with the novel catalysts is distinguished in particular by a low content of phenolic by-products (particularly by a low content of phenol), in the crude products, as is illustrated by the examples.

EXAMPLES

Example 1

Catalyst Preparation

1a) Without Potassium, in Accordance with DE 28 49 002 A1 (Comparison)

1.00 liter (bulk volume) of an α-$Al_2O_3$ support in the form of spheres of 3.0 to 5.0 mm diameter ($x_{50.3}$), with a BET surface area of 9.8 $m^2/g$, an absorbency of 45.1 ml of water per 100 g of support and a bulk density of 812 was impregnated with 366 ml of an aqueous solution containing 10.8 g (corresponding to 0.27 mol) of NaOH. The solution was absorbed completely by the support within a few minutes.

The wet support was dried in a hot ascending strong stream of air. The drying time to constant weight was approximately 15 minutes. The residual moisture content after cooling was about 1% of the absorbency of the support.

The dry support pretreated in this way was impregnated according to its absorbency with 366 ml of an aqueous sodium tetrachloropalladate solution which contained 9.0 g of palladium (corresponding to 0.846 mol), and left to stand for 15 minutes. For reduction of the palladium compound deposited on the support to metallic palladium, the catalyst was covered with a layer of 400 ml of a 10% strength aqueous hydrazine hydrate solution and left to stand for 2 hours. Thereafter, the catalyst was rinsed thoroughly with completely desalinated water until ions of the compounds used in the preparation of the catalyst were no longer detectable in the wash water, which was the case after approx. 10 hours.

Drying was then again carried out to constant weight in a strong hot ascending stream of air.

The Pd-containing catalyst was then impregnated with 366 ml of an aqueous solution containing 9.0 g of vanadium as vanadyl oxalate. Drying of the support in the stream of hot air was carried out as described above. The catalyst was then heat-treated in a tubular oven at 300° C. for 6 hours, during which the oxalate was decomposed.

Finally, the catalyst was impregnated with 366 ml of an aqueous solution containing 3.0 g of lead as lead acetate and dried again in an ascending stream of air.

The finished catalyst contained 9.0 g of Pd, 9.0 g of vanadium and 3.0 g of lead per liter of bulk volume of the support and corresponded to the catalyst from Example 1 in DE 28 49 002 A1.

1b) 0.090% by Weight of Potassium as Potassium Sulfate (According to the Invention)

1.000 kg of a catalyst according to Example 1 was impregnated with a solution of 2.0 g of $K_2SO_4$ in 400 ml of water. The catalyst was then dried to constant weight in a stream of hot air. The catalyst contained 0.037% by weight of sulfur.

1c) 0.0090% by Weight of Potassium as Potassium Sulfate (Comparison)

1.000 kg of a catalyst according to Example 1 was impregnated with a solution of 0.20 g of $K_2SO_4$ in 400 ml of water. The catalyst was then dried to constant weight in a stream of hot air. The catalyst contained 0.0037% by weight of sulfur.

1d) 0.44% by Weight of Potassium as Potassium Sulfate (Comparison)

1.000 kg of a catalyst according to Example 1 was impregnated with a solution of 10.0 g of $K_2SO_4$ in 400 ml of water. The catalyst was then dried to constant weight in a stream of hot air. The catalyst contained 0.18% by weight of sulfur and is therefore in the preferred range of the sulfur content disclosed in EP 1 882 681 A1 of from 0.1 to 1% by weight.

1e) Doping with Sodium as Sodium Sulfate (Comparison)

1.000 kg of a catalyst according to Example 1 was impregnated with a solution of 2.0 g of $Na_2SO_4$ in 400 ml of water. The catalyst was then dried to constant weight in a stream of hot air. The catalyst contained 0.045% by weight of sulfur.

1f) 0.10% by Weight of Potassium as Potassium Chloride (According to the Invention)

1.000 kg of a catalyst according to Example 1 was impregnated with a solution of 2.00 g of KCl in 400 ml of water. The catalyst was then dried to constant weight in a stream of hot air.

Example 2

Hydrogenation of Nitrobenzene

General Experimental Conditions

A tube thermostatically controlled with oil and with an internal diameter of approx. 26 mm, into which a 285 cm high bed of the particular catalyst was introduced, served as the reactor. Before each experiment the catalyst was flushed first with nitrogen and then with hydrogen and was subsequently heated up to 240° C. in a stream of hydrogen of approx. 1,500 Nl/h (normal liters per hour) in the course of 5 hours. Vaporization of nitrobenzene in the stream of hydrogen was then started. The nitrobenzene/hydrogen mixture arrived at the surface of the catalyst bed at approx. 230° C. The specific loading of the catalyst was increased stepwise at the start of each experiment from 0.20 $kg_{nitrobenzene}/(l_{catalyst} \cdot h)$ to 1.0 $kg_{nitrobenzene}/(l_{catalyst} \cdot h)$. This was effected such that at no point did the catalyst become hotter than 400° C. The change in the oil temperature along the reactor tube was approx. ±1 K. The flow rate of the oil along the tube surface was approx. 1.5 m/s.

Any regeneration of the catalyst carried out took place after inertization of the reactor with nitrogen. The reactor was temperature-controlled at 270° C. in the nitrogen stream of 1,500 Nl/h. The nitrogen stream was then reduced stepwise to 0 Nl/h in the course of 12 h and in the same period of time an air stream was increased stepwise from 0 Nl/h to 500 Nl/h. The reactor was charged with 500 Nl/h of air at 270° C. for a further 24 h in order to burn off coking deposits.

The conversions, selectivities and phenol contents were determined by means of gas chromatography.

2a) Catalyst from Example 1a (Comparison)
2aa) First Running Period

The experiment was carried out according to the general experimental conditions. After 750 h increasing of the oil temperature in steps of 5 K per day was started, until an oil temperature of 300° C. was reached. The catalyst achieved an operating time of approx. 1,080 hours, after which the nitrobenzene content of the condensate increased from 0 to approx. 300 ppm and the catalyst then had to be regenerated by burning off. The average selectivity was 99.63%, and the average phenol content in the crude aniline was 194 ppm.

2ab) Second Running Period

In the second running period, that is to say after the regeneration, the operating time increased to approx. 1,340 h. The oil temperature was increased in steps of 5 K per day, starting after 1,000 h, until an oil temperature of 300° C. was reached. The average selectivity was 99.61%, and the average phenol content in the crude aniline was 159 ppm.

2b) Catalyst from Example 1b (According to the Invention)
2ba) First Running Period The experiment was carried out according to the general experimental conditions. After 750 h increasing of the oil temperature in steps of 5 K per day was started, until an oil temperature of 300° C. was reached. The catalyst achieved an operating time of approx. 1,090 hours, after which the nitrobenzene content of the condensate increased from 0 to approx. 300 ppm and the catalyst then had to be regenerated by burning off. The average selectivity was 99.72%, and the average phenol content in the crude aniline was 109 ppm.

2bb) Second Running Period

In the second running period, that is to say after the regeneration, the operating time increased to approx. 1,320 h. The oil temperature was increased in steps of 5 K per day, starting after 1,050 h, until an oil temperature of 300° C. was reached. The average selectivity was 99.74%, and the average phenol content in the crude aniline was 74 ppm.

2bc) Third Running Period

In the third running period, that is to say after the second regeneration, the operating time increased to approx. 1,420 h. The oil temperature was increased in steps of 5 K per day, starting after 1,150 h, until an oil temperature of 300° C. was reached. The average selectivity was 99.79% and the average phenol content in the crude aniline was 50 ppm.

2c) Catalyst from Example 1c (Comparison)

The experiment was carried out according to the general experimental conditions. After 725 h increasing of the oil temperature in steps of 5 K per day was started, until an oil temperature of 300° C. was reached. The catalyst achieved an operating time of approx. 1,100 hours, after which the nitrobenzene content of the condensate increased from 0 to approx. 300 ppm and the catalyst then had to be regenerated by burning off. The average selectivity was 99.70° A, and the average phenol content in the crude aniline was 147 ppm.

2d) Catalyst from Example 1d (Comparison)

The experiment was carried out according to the general experimental conditions. After 580 h increasing of the oil temperature in steps of 5 K per day was started, until an oil temperature of 300° C. was reached. The catalyst achieved an operating time of approx. 870 hours, after which the nitrobenzene content of the condensate increased from 0 to approx. 300 ppm and the catalyst then had to be regenerated by burning off. The average selectivity was 99.92%, and the average phenol content in the crude aniline was 22 ppm.

2e) Catalyst from Example 1e (Comparison)

The experiment was carried out according to the general experimental conditions. After 530 h increasing of the oil temperature in steps of 5 K per day was started, until an oil temperature of 300° C. was reached. The catalyst achieved an operating time of approx. 870 hours, after which the nitrobenzene content of the condensate increased from 0 to approx. 300 ppm and the catalyst then had to be regenerated by burning off. The average selectivity was 99.75%, and the average phenol content in the crude aniline was 98 ppm.

2f) Catalyst from Example 1f (According to the Invention)

The experiment vas carried out according to the general experimental conditions. After 530 h increasing of the oil temperature in steps of 5 K per day was started, until an oil temperature of 300° C. was reached. The catalyst achieved an operating time of approx. 1,150 hours, after which the nitrobenzene content of the condensate increased from 0 to approx. 300 ppm and the catalyst then had to be regenerated by burning off. The average selectivity was 99.86%, and the average phenol content in the crude aniline was 102 ppm.

The following table compares the results with one another.

TABLE

| Example | Catalyst | Doping agent ($g_{doping\ agent}/kg_{catalyst\ precursor\ compound}$) | Operating time (conversion >99.97%) [h] | Average selectivity [%] | Average phenol content [ppm] |
|---|---|---|---|---|---|
| 2aa (comp.) | 1a | — | 1,080 | 99.63 | 194 |
| 2ab (comp.) | 1a (regenerated) | | 1,340 | 99.61 | 159 |
| 2ba (inv.) | 1b | $K_2SO_4$ (2.0) | 1,090 | 99.72 | 109 |
| 2bb (inv.) | 1b (regenerated) | | 1,320 | 99.74 | 74 |
| 2bc (inv.) | 1b (2x regenerated) | | 1,420 | 99.79 | 50 |
| 2c (comp.) | 1c | $K_2SO_4$ (0.20) | 1,100 | 99.70 | 147 |

TABLE-continued

| Example | Catalyst | Doping agent ($g_{doping\ agent}$/$kg_{catalyst\ precursor\ compound}$) | Operating time (conversion >99.97%) [h] | Average selectivity [%] | Average phenol content [ppm] |
|---|---|---|---|---|---|
| 2d (comp.) | 1d | $K_2SO_4$ (10.0) | 870 | 99.92 | 22 |
| 2e (comp.) | 1e | $Na_2SO_4$ (2.0) | 830 | 99.75 | 98 |
| 2f (inv.) | 1f | KCl (2.0) | 1,150 | 99.86 | 102 |

(inv. = according to the invention; comp. = comparison experiment)

As a comparison of catalyst 1a with 1b shows, the phenol content can be reduced significantly by using the catalyst 1b doped with potassium, without the operating time changing adversely (the operating times of 2aa and 2ba and of 2ab and 2bb are the same within the margins of measurement accuracy). A reduction in the potassium content by the factor of 10 again leads to considerably increased phenol contents (cf. 2c and 2ba). At very high potassium contents, the phenol content indeed drops drastically (see 2d), but at the expense of a significantly reduced operating time, which overcompensates the advantage of the reduced formation of phenol. The use of sodium sulfate indeed likewise reduces the phenol values, but at the expense of a shortened operating now (cf. 2e and 2ba). Experiment 2f shows that the effects are not to be attributed to sulfur.

The invention claimed is:

1. A catalyst comprising an α-aluminium oxide ceramic support with a BET surface area of less than 10 m²/g and
   (a) 8.0 g to 50 g of palladium,
   (b) 8.0 g to 50 g of vanadium and
   (c) 2.0 g to 10 g of lead,
   per liter of bulk volume of the α-aluminium oxide, wherein the catalyst is doped with
   (d) potassium in a content of from 0.070% by weight to 0.12% by weight, based on the total weight of the catalyst.

2. The catalyst according to claim 1, in which the catalyst is doped with potassium (d) in the form of potassium sulfate, potassium chloride, potassium hydroxide, potassium carbonate, potassium bicarbonate, potassium bromide; potassium acetate, potassium formate and/or potassium nitrate.

3. The catalyst according to claim 2, in which the catalyst is doped with potassium (d) in the form of potassium sulfate or potassium chloride.

4. A process for the preparation of aromatic amines of the formula

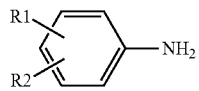

(I)

in which R1 and R2 independently of each other denote hydrogen, methyl or ethyl, wherein R1 can additionally denote $NH_2$, by hydrogenation of nitroaromatics of the formula

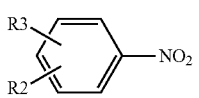

(II)

in which R2 and R3 independently of each other denote hydrogen, methyl or ethyl, wherein R3 can additionally denote $NO_2$,
with hydrogen in the presence of the catalyst according to claim 1.

5. The process according to claim 4, in which aniline is prepared by hydrogenation of nitrobenzene.

6. The process according to claim 4, in which the hydrogenation is carried out isothermally in a reactor with removal of the resulting heat of reaction by a cooling medium.

7. The process according to claim 4, in which
   the molar ratio of hydrogen to nitro groups is 3 to 30:1,
   the absolute pressure at the entry of the reactor is 0.500 bar to 6.00 bar,
   the entry temperature of the gaseous reaction mixture is 200° C. to 460° C., and
   the maximum catalyst temperatures are 600° C.

* * * * *